United States Patent
Vrzalik et al.

(10) Patent No.: US 9,254,231 B2
(45) Date of Patent: Feb. 9, 2016

(54) MULTI-LAYERED SUPPORT SYSTEM

(75) Inventors: John H. Vrzalik, San Antonio, TX (US); Kz Hong, San Antonio, TX (US)

(73) Assignee: HUNTLEIGH TECHNOLOGY LIMITED, Bedfordshire (GB)

( * ) Notice: Subject to any disclaimer, the term of this patent is extended or adjusted under 35 U.S.C. 154(b) by 118 days.

(21) Appl. No.: 13/560,342

(22) Filed: Jul. 27, 2012

(65) Prior Publication Data

US 2013/0025053 A1    Jan. 31, 2013

Related U.S. Application Data (60) Provisional application No. 61/512,609, filed on Jul. 28, 2011.

(51) Int. Cl.
*A61G 7/057* (2006.01)
*A61F 7/08* (2006.01)
*A61F 7/00* (2006.01)

(52) U.S. Cl.
CPC .............. *A61G 7/057* (2013.01); *A61F 7/0097* (2013.01); *A61F 7/08* (2013.01); *A61G 2007/05784* (2013.01)

(58) Field of Classification Search
CPC .......... A61F 7/08; A61F 7/0097; A61G 7/057; A61G 2007/05784
USPC ................. 5/423, 652.2, 726, 941; 607/104
See application file for complete search history.

(56) References Cited

U.S. PATENT DOCUMENTS

| | | | |
|---|---|---|---|
| 2,826,244 A | 3/1958 | Hurley | 5/652.2 |
| 3,735,559 A | 5/1973 | Salemme | 95/52 |
| 4,185,341 A | 1/1980 | Scales | 5/699 |
| 4,483,030 A | 11/1984 | Flick et al. | 5/691 |
| 4,665,575 A | 5/1987 | Raught | 5/722 |
| 4,825,488 A | 5/1989 | Bedford | 5/726 |
| 4,853,992 A | 8/1989 | Yu | 5/423 |
| 4,997,230 A | 3/1991 | Spitalnick | 297/180.11 |
| 5,007,123 A | 4/1991 | Salyards | 5/699 |
| 5,035,014 A | 7/1991 | Blanchard | 5/424 |
| 5,090,074 A | 2/1992 | Scales et al. | 5/699 |
| 5,249,319 A | 10/1993 | Higgs | 5/714 |
| 5,416,935 A | 5/1995 | Nieh | 5/423 |
| 5,473,783 A | 12/1995 | Allen | 5/652.2 |
| 5,498,278 A | 3/1996 | Edlund | 96/11 |
| 5,611,096 A | 3/1997 | Bartlett et al. | 5/617 |

(Continued)

FOREIGN PATENT DOCUMENTS

| | | |
|---|---|---|
| DE | 297 17 879 | 11/1997 |
| DE | 203 06 348 | 9/2003 |

(Continued)

OTHER PUBLICATIONS

AccuMax Quantum Complete, Hill-Rom Services, Inc., copyright 2008-2012. Available online at http://www.woundsource.com/rint/product/accumax-quantum-complete. Accessed Mar. 15, 2012.

(Continued)

*Primary Examiner* — Michael Trettel
(74) *Attorney, Agent, or Firm* — Norton Rose Fulbright US LLP (57) ABSTRACT

In various embodiments, a support system includes a cover sheet with a number of layers. In certain embodiments, a top layer and a bottom layer are bonded to a middle spacer layer.

24 Claims, 5 Drawing Sheets

(56) References Cited

U.S. PATENT DOCUMENTS

| | | | | |
|---|---|---|---|---|
| 5,640,728 | A | 6/1997 | Graebe | 5/606 |
| 5,647,079 | A | 7/1997 | Hakamiun et al. | 5/713 |
| 5,681,368 | A | 10/1997 | Rahimzadeh | 95/52 |
| 5,701,621 | A | 12/1997 | Landi et al. | 5/691 |
| 5,755,000 | A | 5/1998 | Thompson | 5/713 |
| 5,882,349 | A | 3/1999 | Wilkerson et al. | 604/289 |
| 5,887,304 | A | 3/1999 | Von der Heyde | 5/726 |
| 5,926,884 | A | 7/1999 | Biggie et al. | 5/714 |
| 6,065,166 | A | 5/2000 | Sharrock et al. | 5/630 |
| 6,085,369 | A | 7/2000 | Feher | 5/423 |
| 6,182,315 | B1 | 2/2001 | Lee | 5/690 |
| 6,272,707 | B1 | 8/2001 | Robrecht et al. | 5/724 |
| 6,288,076 | B1 | 9/2001 | Kostyniak et al. | 514/299 |
| 6,336,237 | B1 | 1/2002 | Schmid | 5/726 |
| 6,341,395 | B1 | 1/2002 | Chao | 5/423 |
| 6,353,950 | B1 | 3/2002 | Bartlett et al. | 5/617 |
| 6,418,579 | B2 | 7/2002 | Perez et al. | 5/713 |
| 6,421,859 | B1 | 7/2002 | Hicks et al. | 5/722 |
| 6,487,739 | B1 | 12/2002 | Harker | 5/729 |
| 6,493,889 | B2 | 12/2002 | Kocurek | 5/423 |
| 6,527,832 | B2 | 3/2003 | Oku et al. | 96/4 |
| 6,546,576 | B1 | 4/2003 | Lin | 5/423 |
| 6,671,911 | B1 | 1/2004 | Hill et al. | 5/713 |
| 6,687,937 | B2 | 2/2004 | Harker | 5/726 |
| 6,709,492 | B1 | 3/2004 | Spadaccini et al. | 96/6 |
| 6,779,592 | B1 | 8/2004 | Ichigaya | 165/46 |
| 6,782,574 | B2 | 8/2004 | Totton et al. | 5/726 |
| 6,868,569 | B2 | 3/2005 | VanSteenburg | 5/709 |
| 6,904,629 | B2 | 6/2005 | Wu | 165/46 |
| 7,036,163 | B2 | 5/2006 | Schmid | 5/423 |
| 7,043,767 | B2 | 5/2006 | Jaeger | 2/87 |
| 7,100,978 | B2 * | 9/2006 | Ekern et al. | 297/180.11 |
| 7,140,495 | B2 | 11/2006 | Hester et al. | 210/490 |
| 7,165,281 | B2 | 1/2007 | Larssson et al. | 5/724 |
| 7,191,482 | B2 | 3/2007 | Romano et al. | 5/714 |
| 7,240,386 | B1 | 7/2007 | McKay et al. | 5/724 |
| 7,290,300 | B1 | 11/2007 | Khambete | 5/423 |
| 7,296,315 | B2 | 11/2007 | Totton et al. | 5/737 |
| 7,311,685 | B1 | 12/2007 | Policastro | 602/3 |
| 7,334,280 | B1 | 2/2008 | Swartzburg | 5/724 |
| 7,357,830 | B2 | 4/2008 | Weidmann | 95/52 |
| 7,469,432 | B2 * | 12/2008 | Chambers | 5/423 |
| 7,480,953 | B2 | 1/2009 | Romano et al. | 5/714 |
| 7,631,377 | B1 | 12/2009 | Sanford | 5/423 |
| 7,637,573 | B2 | 12/2009 | Bajic et al. | 297/452.43 |
| 7,712,164 | B2 | 5/2010 | Chambers | 5/423 |
| 7,886,385 | B2 | 2/2011 | Carlitz | 5/691 |
| 7,913,332 | B1 | 3/2011 | Barnhart | 5/423 |
| 7,914,611 | B2 | 3/2011 | Vrzalik et al. | 96/11 |
| 7,937,789 | B2 | 5/2011 | Feher | 5/421 |
| 7,937,791 | B2 | 5/2011 | Meyer et al. | 5/727 |
| 7,966,680 | B2 | 6/2011 | Romano et al. | 5/713 |
| 7,975,331 | B2 * | 7/2011 | Flocard et al. | 5/423 |
| 8,118,920 | B2 | 2/2012 | Vrzalik et al. | 96/11 |
| 8,327,478 | B2 * | 12/2012 | Faridoon | 5/423 |
| 2001/0023512 | A1 | 9/2001 | Perez et al. | 5/713 |
| 2002/0073489 | A1 | 6/2002 | Totton et al. | 5/713 |
| 2002/0129449 | A1 | 9/2002 | Harker | 5/726 |
| 2002/0148047 | A1 | 10/2002 | Corzani et al. | 5/738 |
| 2003/0019044 | A1 | 1/2003 | Larsson et al. | 5/724 |
| 2003/0145380 | A1 | 8/2003 | Schmid | 5/423 |
| 2004/0003471 | A1 | 1/2004 | VanSteenburg | 5/709 |
| 2004/0064888 | A1 | 4/2004 | Wu | 5/423 |
| 2004/0214495 | A1 | 10/2004 | Foss et al. | 442/144 |
| 2004/0237203 | A1 | 12/2004 | Romano et al. | 5/713 |
| 2005/0011009 | A1 | 1/2005 | Wu | 5/729 |
| 2005/0022308 | A1 | 2/2005 | Totton et al. | 5/713 |
| 2005/0086739 | A1 | 4/2005 | Wu | 5/423 |
| 2005/0188467 | A1 | 9/2005 | Woolfson | 5/726 |
| 2005/0278863 | A1 | 12/2005 | Bahash et al. | 5/726 |
| 2006/0010607 | A1 | 1/2006 | Schneider | 5/713 |
| 2006/0080778 | A1 | 4/2006 | Chambers | 5/652.2 |
| 2007/0056116 | A1 | 3/2007 | Galardo | 5/724 |
| 2007/0234481 | A1 | 10/2007 | Totton et al. | 5/714 |
| 2007/0261548 | A1 | 11/2007 | Vrzalik et al. | 96/11 |
| 2007/0266499 | A1 | 11/2007 | O'Keefe et al. | 5/713 |
| 2007/0283498 | A1 | 12/2007 | Shelby | 5/706 |
| 2008/0022461 | A1 | 1/2008 | Bartlett et al. | 5/714 |
| 2008/0028536 | A1 | 2/2008 | Hadden-Cook | 5/724 |
| 2008/0060131 | A1 | 3/2008 | Tompkins | 5/423 |
| 2008/0098529 | A1 | 5/2008 | Flocard et al. | 5/652.2 |
| 2008/0263776 | A1 | 10/2008 | O'Reagan et al. | 5/714 |
| 2009/0322124 | A1 | 12/2009 | Barkow et al. | 297/180.14 |
| 2010/0043143 | A1 | 2/2010 | O'Reagan et al. | 5/421 |
| 2010/0095461 | A1 | 4/2010 | Romano et al. | 5/710 |
| 2010/0122417 | A1 | 5/2010 | Vrzalik et al. | 5/652.1 |
| 2010/0175196 | A1 | 7/2010 | Lafleche et al. | 5/707 |
| 2010/0287701 | A1 | 11/2010 | Frias | 5/423 |
| 2011/0004997 | A1 | 1/2011 | Hale et al. | 5/699 |
| 2011/0010850 | A1 | 1/2011 | Frias | 5/423 |
| 2011/0010855 | A1 | 1/2011 | Flessate | 5/484 |
| 2011/0035880 | A1 | 2/2011 | Cole et al. | 5/423 |
| 2011/0107514 | A1 | 5/2011 | Brykalski et al. | 5/421 |
| 2011/0154575 | A1 | 6/2011 | Kiser | 5/706 |

FOREIGN PATENT DOCUMENTS

| | | |
|---|---|---|
| DE | 203 09 793 | 10/2003 |
| DE | 203 09 794 | 10/2003 |
| EP | 0 870 449 | 10/1998 |
| EP | 1 151 698 | 11/2001 |
| EP | 1 645 258 | 4/2006 |
| EP | 1 687 139 | 8/2006 |
| EP | 1 863 369 | 12/2007 |
| EP | 1 901 636 | 3/2008 |
| EP | 1 919 328 | 5/2008 |
| EP | 1 971 246 | 9/2008 |
| EP | 2 047 770 | 4/2009 |
| EP | 2 258 242 | 12/2010 |
| EP | 2 305 200 | 4/2011 |
| EP | 2 319 474 | 5/2011 |
| GB | 2 235 872 | 3/1991 |
| JP | H02-11144 | 1/1990 |
| JP | 11-164757 | 6/1999 |
| JP | 11-169262 | 6/1999 |
| JP | 11-332697 | 12/1999 |
| JP | 2000-152854 | 6/2000 |
| JP | 2002-125809 | 5/2002 |
| JP | 2003-230605 | 8/2003 |
| JP | 2004-188052 | 8/2004 |
| WO | WO 2004/082551 | 9/2004 |
| WO | WO 2005/046988 | 5/2005 |
| WO | WO 2006/122614 | 4/2006 |
| WO | WO 2006/105169 | 10/2006 |
| WO | WO 2007/003018 | 1/2007 |
| WO | WO 2007/034311 | 3/2007 |
| WO | WO 2008/098945 | 8/2008 |
| WO | WO 2011/067720 | 6/2011 |

OTHER PUBLICATIONS

Gaymar SPR-Plus, Pressure Distributing Low Air Loss System, Gaymar Industries, Inc. Product Brochure. Copyright 2009. Available online at http://www.gaymar.com/wesstore/ExtendedSitesCatalogAssetStore/pdf/SPR_Plus_New_5.pdf., Accessed Mar. 15, 2012.

PCT International Search Report and Written Opinion issued in International application No. PCT/US2011/038147, dated Oct. 5, 2011.

Span American PressureGuard Easy Air Low Air Loss Product, Span America, Product Page, Copyright 2012. Available online at http://www.spanamerica.com/easy_air.php. Accessed Mar. 15, 2012.

Extended European Search Report issued in European Patent Application No. 12181372.9, dated Oct. 1, 2012.

International Search Report and Written Opinion issued in PCT Application No. PCT/US2012/048468, mailed Oct. 10, 2012.

Office Communication issued in Canadian Patent Application No. 2,651,960, dated Dec. 12, 2011.

Office Communication issued in Japanese Patent Application No. 2009-510186, dated Oct. 25, 2011. (English summary of Japanese document provided).

(56) References Cited

OTHER PUBLICATIONS

Office Communication issued in U.S. Appl. No. 13/048,642, dated Jun. 16, 2011.
Office Communication, issued in Australian Patent Application No. 2007249236, dated Mar. 17, 2011.
Office Communication, issued in Chinese Patent Application No. 200780016996.3, dated Mar. 1, 2010. (English translation of Chinese document provided).
Office Communication, issued in European Patent Application No. EP07783677, dated Feb. 15, 2011.
Office Communication, issued in European Patent Application No. EP07783677, dated Oct. 12, 2011.
Office communication, issued in Japanese Patent Application No. 2009-510186, mailed on Apr. 10, 2012.
Office Communication, issued in U.S. Appl. No. 11/746,953, dated Aug. 11, 2010.
Office Communication, issued in U.S. Appl. No. 11/746,953, dated Feb. 25, 2010.
PCT International Preliminary Report on Patentability issued in International Application No. PCT/US07/68801, dated Nov. 11, 2008.
PCT International Search Report issued in International Application No. PCT/US07/68801, dated Nov. 2, 2007.
Reger et al., "Validation test for climate control on air loss supports," *Arch. Phys. Med. Rehab.*, 82:597-603, 2001.
Extended European Search Report issued in European Application No. 09828235, dated Sep. 21, 2012.

\* cited by examiner

MULTI-LAYERED SUPPORT SYSTEM

CROSS-REFERENCE TO RELATED APPLICATIONS

This application claims priority to U.S. Provisional Patent Application Ser. No. 61/512,609, filed Jul. 28, 2011, the entire contents of which are incorporated herein by reference.

FIELD OF THE INVENTION

The present disclosure relates generally to support surfaces for independent use and for use in association with beds and other support platforms, and more particularly but not by way of limitation to support surfaces that aid in the prevention, reduction, and/or treatment of decubitus ulcers and the transfer of moisture and/or heat from the body.

BACKGROUND

Patients and other persons restricted to bed for extended periods incur the risk of forming decubitus ulcers. Decubitus ulcers (commonly known as bed sores, pressure sores, pressure ulcers, etc.) can be formed when blood supplying the capillaries below the skin tissue is interrupted due to external pressure against the skin. This pressure can be greater than the internal blood pressure within a capillary and thus, occlude the capillary and prevent oxygen and nutrients from reaching the area of the skin in which the pressure is exerted. Moreover, moisture and heat on and around the person can exacerbate ulcers by causing skin maceration, among other associated problems.

SUMMARY

Exemplary embodiments of the present disclosure are directed to apparatus, systems and methods to aid in the prevention of decubitus ulcer formation and/or promote the healing of such ulcer formation.

In various embodiments, a support system includes a cover sheet with a number of layers. In certain embodiments, a top layer and a bottom layer are bonded to a middle spacer layer.

Particular embodiments may include a cover sheet comprising a first end, a second end, a first side and a second side. In certain embodiments, the cover sheet may comprise an air mover; a first layer comprising a vapor permeable material; a second layer comprising a spacer material; and a third layer. In specific embodiments, the second layer may be between the first layer and the third layer, the air mover may be configured to create air flow through the spacer material, and the first layer may be substantially bonded to the second layer in a region between the first and second ends and between the first and second sides.

In particular embodiments, the third layer may be substantially bonded to the second layer in a region between the first and second ends and between the first and second sides. In specific embodiments, the air mover may be in fluid communication with a first aperture in the first or third layer, and in certain embodiments, the first aperture may be proximal to the first end of the cover sheet. Particular embodiments may also comprise a second aperture in the first or third layer where the second aperture is proximal to the second end of the cover sheet.

In certain embodiments, the air mover may be proximal to the first end of the cover sheet, and the second layer may be open to an outside environment proximal to the second end of the cover sheet. In particular embodiments, the air mover may be configured to generate positive air pressure between the first layer and the third layer of the cover sheet. In specific embodiments, the first layer and the third layer may be air impermeable.

In particular embodiments, the spacer material may comprise one of the following: open cell foam; natural or synthetic polymer particles, filaments, or strands; mesh; cotton fibers; polyester fibers; flexible metals and metal alloys; shape memory metals and metal alloys, and shape memory plastics. Certain embodiments may also comprise an antimicrobial device proximal to the air mover. In particular embodiments, the spacer material may comprise an antimicrobial agent.

In specific embodiments, the air mover may be configured to provide less than about 2.0 cubic feet per minute of air flow at a differential pressure of less than about 6.0 mm H2O. In certain embodiments, the air mover may be configured to provide less than about 10.0 cubic feet per minute of air flow at a differential pressure of less than about 6.0 mm H2O, and may be configured to create noise levels of approximately 30.0 dB-A during operation. In specific embodiments, the air mover may be a centrifugal fan. Certain embodiments may further comprise an antimicrobial device proximal to the air mover, and in particular embodiments, the air mover may be integral with the cover sheet. In certain embodiments, the spacer material may be configured to permit air to flow through the spacer material while the spacer material supports a person laying on the cover sheet.

Particular embodiments may also comprise a method of removing moisture vapor from a person. In certain embodiments, the method may comprise providing a cover sheet between a support surface and a person, where the cover sheet comprises an air mover, and operating the air mover to provide an air flow through the spacer material.

In certain embodiments, the cover sheet may comprise: a first end, a second end, a first side and a second side; a first layer comprising a vapor permeable material; a second layer comprising a spacer material; and a third layer and operating the air mover to provide an air flow through the spacer material. In specific embodiments, the second layer may be between the first layer and the third layer, and in particular embodiments, the first layer may be substantially bonded to the second layer in a region between the first and second ends and between the first and second side. In particular embodiments, the third layer may be substantially bonded to the second layer in a region between the first and second ends and between the first and second sides.

In specific embodiments of the method, the air flow may be directed away from the air mover. In particular embodiments of the method, the spacer material may comprise one of the following: open cell foam; natural or synthetic polymer particles, filaments, or strands; mesh; cotton fibers; polyester fibers; flexible metals and metal alloys; shape memory metals and metal alloys, and shape memory plastics. In certain embodiments of the method, the air mover may be proximal to the first end and the air flow may exit from the spacer material proximal to the second end. In specific embodiments of the method, the air mover may be integral with the cover sheet.

BRIEF DESCRIPTION OF THE DRAWINGS

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, portions of the support system shown and described may be incorporated with existing mattresses or support materials. Other embodiments may utilize the support system in seating applications, including but not limited to, wheelchairs, chairs, recliners, benches, etc.

In the following Detailed Description of Disclosed Embodiments, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed embodiment. Thus, the following claims are hereby incorporated into the Detailed Description of Disclosed Embodiments, with each claim standing on its own as a separate embodiment.

DETAILED DESCRIPTION OF DISCLOSED EMBODIMENTS

Exemplary embodiments of the present disclosure are directed to apparatus, systems and methods to aid in the prevention of decubitus ulcer formation and/or promote the healing of such ulcer formation. For example, in various embodiments, preventing ulcer formation and/or healing decubitus ulcers can be accomplished through the use of a multi-layer cover sheet. Exemplary embodiments of the multi-layer cover sheet can be utilized to aid in the removal of moisture, vapor, and heat adjacent and proximal the patient surface interface and in the environment surrounding the patient by providing a surface that absorbs and/or disperses the moisture, vapor, and heat from the patient. In addition, the exemplary embodiments of the multi-layer cover sheet can be utilized in combination with a number of support surfaces or platforms to provide a reduced interface pressure between the patient and the cover sheet on which the patient is positioned. This reduced interface pressure can help to prevent the formation of decubitus ulcers.

In various exemplary embodiments, the cover sheet may include a number of layers. Each layer may be formed of a number of different materials that exhibit various properties. These properties may include the level of friction or shear of a surface, the permeability of a vapor, a gas, a liquid, and/or a solid, and various phases of the vapor, the gas, the liquid, and the solid, and other properties.

For example, in exemplary embodiments, the multi-layer cover sheet may include materials that provide for a low air loss feature, where one or more layers exhibit various air, vapor, and liquid permeable properties and/or where one or more layers are bonded or sealed together. As used herein, a low air loss feature of a multi-layer cover sheet includes, but is not limited to: a multi-layer cover sheet that allows air and vapor to pass through the first or top layer in the presence of a partial pressure difference in vapor between the internal and external environments of the multi-layer cover sheet; a multi-layer cover sheet that allows air and vapor to pass through the first layer in the absence of a partial pressure difference in vapor between the internal and external environments of the multi-layer cover sheet; and a multi-layer cover sheet that allows air and vapor to move into and/or out of the multi-layer cover sheet through the apertures in one or more layers.

In other exemplary embodiments, the multi-layer cover sheet can include materials that provide for substantially no air flow, where one or more layers include air impermeable properties and/or where layers are bonded or sealed together to a layer comprising a spacer material. In such exemplary embodiments, this configuration may control the direction of movement of air from inside to outside (e.g., under influence by a source of positive pressure at the air inlet at the air mover for the cover sheet) and from outside to inside (e.g., under influence by a source of negative pressure at the air inlet at the air mover for the cover sheet) the multi-layer cover sheet. Certain exemplary embodiments comprise a multi-layer cover sheet including, but is not limited to, the following: a cover sheet that prevents or substantially prevents air from passing through the first layer, but allows for the passing of vapor through the first layer; a cover sheet that prevents or substantially prevents air from moving through the first layer in the presence of a partial vapor pressure difference between the internal and external environments of the multi-layer cover sheet, but allows for the passing of vapor through the first layer; and a cover sheet that prevents or substantially prevents air from moving out of the multi-layer cover sheet via the material forming a particular layer of the cover sheet, but allows air to move through the apertures in one or more layers.

In various exemplary embodiments, systems are provided that can include a number of components that both aid in prevention of decubitus ulcer formation and to remove moisture and/or heat from the patient. For example, systems can include a multi-layer cover sheet that can be used in conjunction with a variety of support surfaces, such as an inflatable mattress, a foam mattress, a gel mattress, a water mattress, or a RIK® Fluid Mattress of a hospital bed. In such exemplary embodiments, features of the multi-layer cover sheet can help to remove moisture from the patient and to lower interface pressure between a patient and the surface of the multi-layer cover sheet, while features of the inflatable or foam mattress can aid in the prevention and/or healing of decubitus ulcers by further lowering interface pressures at areas of the skin in which external pressures are typically high, as for example, at bony prominences such as the heel and the hip area of the patient. In other exemplary embodiments, systems can include the multi-layer cover sheet used in conjunction with a chair or other support platform.

Figure 1:
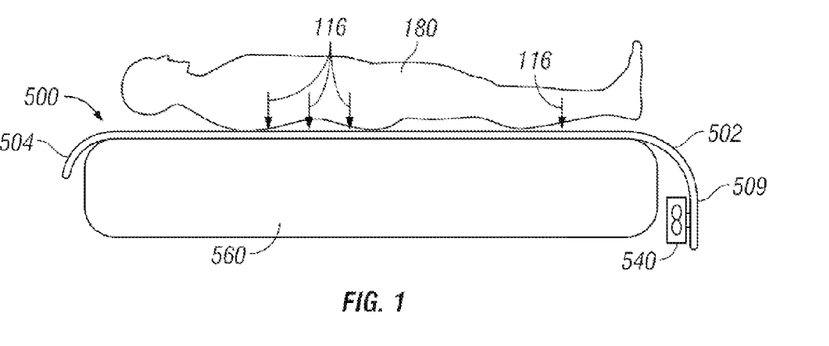
FIG. 1 illustrates a side view of a first exemplary embodiment of a cover sheet and a support mattress supporting a person.
Figure 2A:
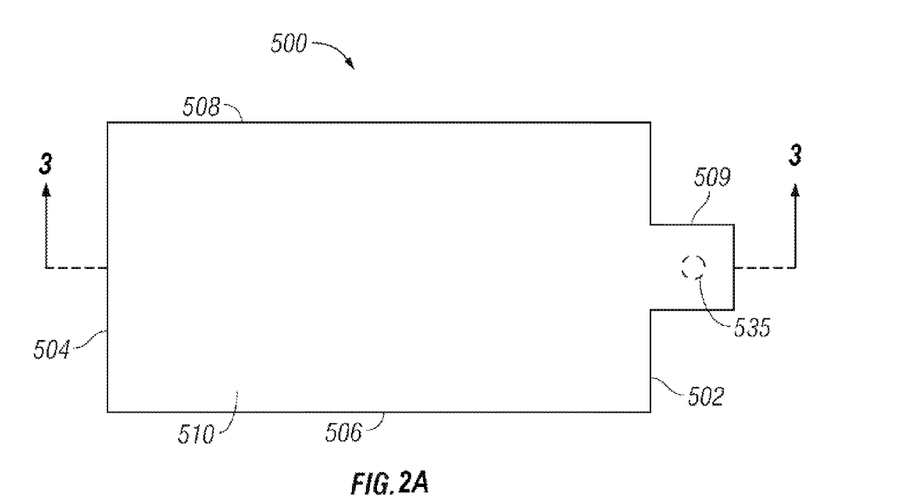
FIG. 2A illustrates a top view of an exemplary embodiment of the cover sheet of FIG. 1.
Figure 2B:
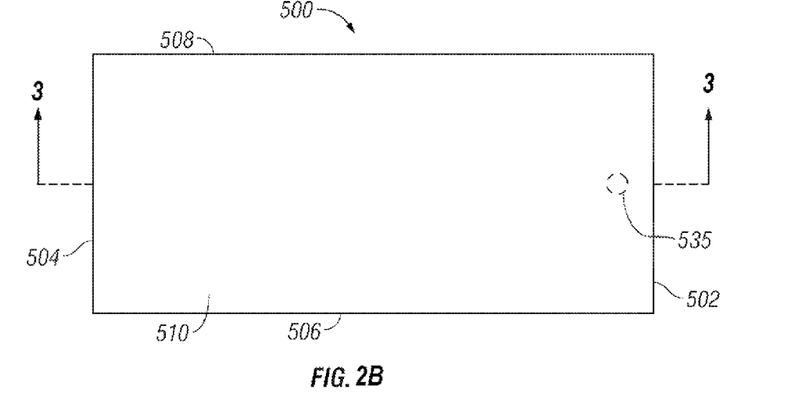
FIG. 2B illustrates a top view of an exemplary embodiment of the cover sheet of FIG. 1.
Figure 3:
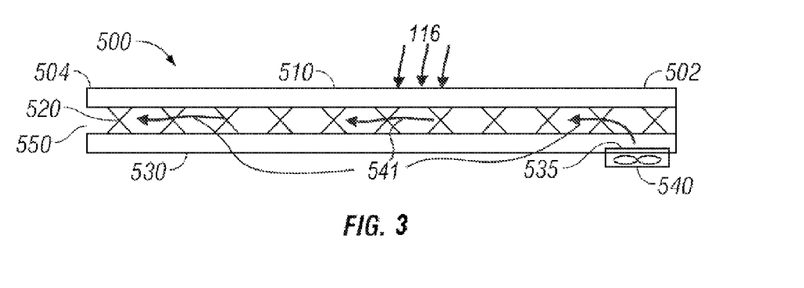
FIG. 3 illustrates a cross-sectional side view of the cover sheet of FIG. 1.

Referring now to FIGS. 1-3, an exemplary embodiment of a cover sheet 500 comprises a first end 502, a second end 504, a first side 506, a second side 508. FIG. 1 illustrates a side view of cover sheet 500 during use and located between a patient 180 and supporting mattress 560. FIGS. 2A and 2B provide a top views of exemplary embodiments of cover sheet 500, while FIG. 3 provides a section view of cover sheet 500 taken along line 3-3 in FIGS. 2A and 2B.

The exemplary embodiments shown comprise a water vapor-permeable upper layer 510 (which may be a composite of many layers), a middle layer 520 comprising a spacer material, and a lower layer 530. In the embodiments shown, upper and lower layers 510, 530 are substantially bonded to middle layer 520 in a region between first and second ends 502, 504 and between first and second sides 506, 508.

In this embodiment, cover sheet 500 also comprises an aperture 535 in lower layer 530 and proximal to first end 502, as well as an air mover 540 in fluid communication with aperture 535. In the exemplary embodiment shown in FIG. 2A, aperture 535 and air mover 540 are located in a tab or extension 509 that allows air mover 540 to be placed near the end of a supporting mattress 560. In the embodiment shown in FIG. 2B, cover sheet 500 does not comprise an extension for air mover 540, and air mover 540 may instead be in fluid communication with aperture 535 in the main body (e.g., proximal to first end 502) of cover sheet 500. In other embodiments (not shown) air mover 540 may be installed along one side of cover sheet 500 and cover sheet 500 may be configured to direct air flow to high pressure contact areas, including for example, the trocantor, sacrum, scapula and heels of a person being supported.

The general principles of operation for this exemplary embodiment are provided initially, followed by a more detailed description of individual components and principles of operation. In general, moisture vapor 116 is transferred from a patient 180, through upper layer 510, to air contained in middle layer 520. Air mover 540 pushes or pulls air through middle layer 520 so that moisture vapor can be removed from the air contained in middle layer 520.

In this exemplary embodiment, upper layer 510 and lower layer 530 are sealed or bonded to middle layer 520 substantially across the entire surface of the middle layer 520 between first end 502, second 504, first side 506 and second side 508. In particular embodiments, upper layer 510 and lower layer 530 may be bonded to middle layer via heat sealing, gluing, mechanical fastening, or other suitable methods. In certain embodiments in which middle layer 520 is an open cell foam, lower layer 530 (and/or upper layer 510) may comprise the "skin" or sealed outer layer that is formed when the open cell foam is cured during the manufacturing process.

In the embodiment shown, upper layer 510 and lower layer 530 are substantially the same size as middle layer 520 so that there are no gaps or spaces around the outer edges of middle layer 520. With upper layer 510 and lower layer 530 bonded to middle layer 520, air flow 541 provided by air mover 540 is directed through middle layer 520.

If upper layer 510 and lower layer 530 were not bonded to middle layer 520, air flow 541 could be allowed to flow through a space between upper layer 510 and middle layer 520, and/or a space between lower layer 530 and middle layer 520. Allowing air flow 541 to flow through such spaces and essentially bypass middle layer 520 can dramatically reduce the ability to remove moisture vapor 116 from middle layer 520.

The tendency of air flow 541 to bypass middle layer 520 can be particularly problematic when air mover 541 is configured to provide positive pressure to cover sheet 500, especially at higher air flow rates. Such a configuration increases the pressure between upper layer 510 and lower layer 530, which can result in billowing of upper layer 510 if it is not bonded to middle layer 520. Upper layer 510 can be particularly prone to billowing in the areas that are not directly under patient 180 if it is not bonded to middle layer 520. The bonding of upper layer 510 and/or lower layer 530 may also be particularly beneficial when cover sheet 500 is used in conjunction with existing support systems that provide an existing source of positive air pressure for cover sheet 500 but do not have a readily-available source of negative air pressure. In embodiments in which cover sheet 500 utilizes negative air pressure, the bonding of upper layer 510 can be beneficial to reduce or prevent upper layer 510 from forming creases which may come into contact with person 180.

Air flow 541 will flow from areas of higher pressure to lower pressure and follow the path of least resistance. If spaces are allowed to form between upper layer 510 and middle layer 520 that provide less resistance than middle layer 520, air flow 541 can flow through such spaces rather than middle layer 520. Therefore, if billowing of upper layer 510 is allowed to create open spaces above or below middle layer 520, air flow 541 will substantially bypass middle layer 520 and reduce the ability of cover sheet 500 to remove moisture vapor 116.

In the exemplary embodiment shown, upper layer 510 and lower layer 530 form a shell or envelope that substantially encases middle layer 520 and forces air flow 541 to be directed through middle layer 520. In the embodiment shown, second end 504 comprises an aperture 550 that allows air flow 541 to exit middle layer 520 and exhaust to the outside environment. By placing aperture 550 distal from air mover 540, air flow 541 is forced to flow through substantially the entire length of middle layer 520. This can maximize the ability of cover sheet 500 to remove moisture vapor 116.

In the exemplary embodiment shown in FIGS. 1-3, aperture 550 may be formed so that middle layer 520 is exposed to the outside environment along the entire second end 504. In other embodiments, second end 504 may be partially sealed (i.e. upper layer 510 and lower layer 530 may be connected along a portion of second end 504) so that a portion of middle layer 520 proximal to second end 504 is exposed to the outside environment to form aperture 550. In certain exemplary embodiments, aperture 550 may be formed by removing material from either upper layer 510 or lower layer 530 (e.g., by cutting a slit or hole in either of the layers, or by providing a strip of air permeable material in upper layer 510 or lower layer 530 proximal end 504).

Second end 504 may be partially sealed so that a second aperture similar to aperture 535 is provided at second end 504. In such embodiments, air mover 540 may be placed at either first end 502 or second end 504 of cover sheet 500. Such a configuration can provide flexibility in the configuration of cover sheet 500 by allowing air mover 540 to be placed at either first end 502 or second end 504, thereby allowing air mover 540 to be placed at either the head end or the foot end of the patient and distal from aperture 550. In other embodiments, air mover 540 may be placed in a different location, and middle layer 520 may be exposed to the outside environment in locations other than first end 502 or second end 504.

Figure 6:
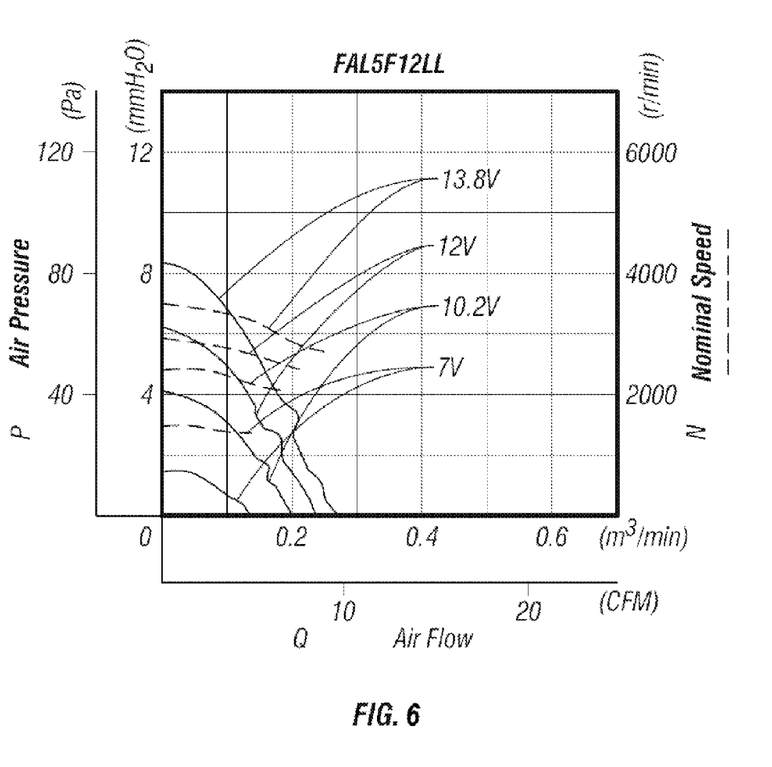
FIG. 6 illustrates a graph of air pressure versus flow for an embodiment of an air mover in one exemplary embodiment.

In certain exemplary embodiments, air mover 540 is a centrifugal 12 volt (nominal) DC fan manufactured by Panasonic under the part number FAL5F12LL. This particular air mover is approximately 3 inches wide by 3 inches tall by 1.1 inches thick and weighs approximately 3.5 ounces. This air mover also produces a maximum air flow of approximately 8.8 cfm and maximum air pressure of approximately 6.2 $mmH_2O$ at a nominal 12 volts. During operation, the air flow will be reduced as the pressure across the air mover is increased. Exemplary embodiments using this air mover typically have an air flow of approximately 1.0 to 2.0 cfm during operation. A graph of air pressure, air flow, and nominal speed for various voltages is provided in FIG. 6. As shown in FIG. 6, this air mover provides less than 6 mmH2O differential pressure at flow rates of approximately 2.0 cfm. The Panasonic FAL5F12LL air mover also creates low noise levels (30.0 dB-A, according to the manufacturer's specifications).

In another exemplary embodiment, air mover 540 is a 12 volt DC, 40 mm box fan such as a Sunon KDE 1204 PKBX-8. By utilizing an air mover such as the Sunon model (or other similarly-sized devices), air mover 540 can be placed integral to cover sheet 500, allowing for a more compact overall design.

In still other exemplary embodiments, upper layer 510 and lower layer 530 may be comprised of the same material and configured to form a shell that contains middle layer 520. In other exemplary embodiments, upper layer 510 may comprise a section of material with high vapor permeability in the center section (closest to a person's trunk) and materials with lower vapor permeability (and perhaps lower cost) in the side areas not directly underneath a person's trunk. In certain exemplary embodiments, upper layer 510 may also be air permeable to allow air to flow through upper layer 510 in addition to an opening between upper layer 510 and lower layer 530.

Figure 4A:
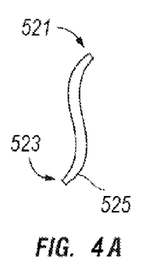
FIGS. 4A-4D illustrate various exemplary embodiments of a spacer material of the cover sheet of FIG. 1.
Figure 4B:
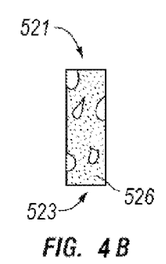
Figure 4C:
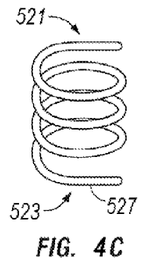
Figure 4D:
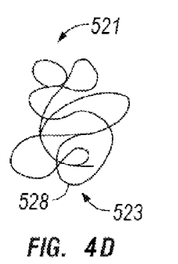

In this embodiment, upper layer 519 is comprised of a material that is liquid impermeable and vapor permeable and either air permeable or impermeable. One example of such vapor permeable material is sold under the trade name GoreTex.™ GoreTex™ is vapor permeable and liquid impermeable, but may be air permeable or air impermeable. Examples of such vapor impermeable materials include sheet vinyl or sheet urethane. In the embodiment shown, middle layer 520 comprises a spacer material that separates upper layer 510 and lower layer 530. As used in this disclosure, the term "spacer material" (and related terms) should be construed broadly to include any material that includes a volume of air within the material and allows air to move through the material. In exemplary embodiments, spacer materials allow air to flow through the material when a person is laying on the material while the material is supported by a mattress. Examples of such spacer materials include open cell foam, polymer particles, and a material sold by Tytex under the trade name AirX™. Additional examples and features of spacer materials are disclosed in the description of second layer 520 in FIGS. 4A-4C. In the exemplary embodiment shown, lower layer 530 comprises a material that is vapor impermeable, air impermeable, and liquid impermeable. Examples of such material include sheet vinyl plastic or sheet polyurethane material. Upper layer 510 and lower layer 530 may be comprised of the same material in certain embodiments.

Referring back to FIG. 1, supporting mattress 560 and cover sheet 500 system provide support for person 180 and aids in the removal of moisture, vapor and heat adjacent and proximal the interface between person 180 and supporting mattress 560. In the exemplary embodiment of FIG. 1, cover sheet 500 comprises an integral air mover 540. In other exemplary embodiments, air mover 540 may be external to cover sheet 500 with appropriate coupling members such as tubing, piping or duct work, etc. In certain exemplary embodiments, air mover 540 may comprise a guard or other partition (not shown) to prevent material from cover sheet 500 or the surrounding environment from blocking the inlet or outlet of air mover 540. During operation, air mover 540 shown in FIG. 1 operates to increase pressure within cover sheet 500 and create a positive air flow 541 that is pushed or forced through middle layer 520 and into the surrounding environment.

In the exemplary embodiments shown in FIGS. 1-3, moisture vapor 116 is transferred from person 180 (and the air adjacent person 180) through upper layer 510 to air pockets within the spacer material of middle layer 520. Moisture vapor 116 will continue to transfer to air pockets within spacer material 122 while the air pockets are at a lower relative humidity than the air adjacent person 180. As the relative humidity of the air pockets increases and approaches the relative humidity of the air adjacent person 180, the transfer rate of moisture vapor 116 will decrease. It is therefore desirable to maintain a lower relative humidity of the air pockets within middle layer 520 than the relative humidity of the air adjacent person 180. As moisture vapor 116 is transferred to air pockets within middle layer 520, it is desirable to remove moisture vapor from the air pockets and lower the relative humidity of the air within middle layer 520. By removing moisture vapor 116 from the air within middle layer 520, the transfer rate of moisture vapor 116 from person 180 can be maintained at a more uniform level.

In the exemplary embodiment shown in FIG. 3, air flow 541 flows through the air pockets within middle layer 520 and assists in removing moisture vapor 116 from the air pockets. This lowers the relative humidity of the air pockets and allows the transfer rate of moisture vapor 116 to be maintained over time. As shown in FIG. 3, air flow 541 can be forced from air mover 540 to enter the air space within middle layer 520. By forcing substantially all of air flow 541 to be directed through middle layer 520, the amount of air flow required for a give moisture vapor transfer rate can be reduced as compared to systems that allow air flow to bypass the second layer.

The reduction in the amount of air flow 541 for a given transfer rate of moisture vapor 116 reduces the size required for the air mover 540. A sufficient reduction in the size of air mover 540 may allow for air mover 540 to be placed in locations that would otherwise not be possible. In one exemplary embodiment, air mover 540 may be coupled to lower layer 530 with a substantially airtight seal so that air does not flow around air mover 540 is directed to middle layer 520. As shown in the embodiment of FIG. 1, air mover 540 may be incorporated into an area of cover sheet 500 that is near the end of support mattress 160. By placing air mover 540 in a location that is not between support mattress 560 and patient 180, the comfort of patient 180 should not be adversely affected. In other embodiments, air mover 540 may be placed in other areas of cover sheet 500. For example, in embodiments where air mover 540 is sufficiently small, air mover 540 may be placed between patient 180 and support mattress 160 without adversely affecting the comfort of patient 180.

A decrease in the required air flow 541 can also reduce the amount of energy required to operate air mover 540, thereby reducing operating costs. Reduced energy requirements and air flow 541 from air mover 540 can also reduce the amount of noise and heat generated by air mover 540. A reduction in noise and heat can provide a more comfortable environment for person 180, who may use cover sheet 500 for extended periods of time.

A reduction in the size of air mover 540 may also lead to a reduction in the cost of air mover 540. In certain embodiments, the cost of air mover 540 may be low enough for air mover 540 to be a disposable item. In addition, cover sheet 500 can be configured to be disposable or reusable. In exemplary embodiments comprising a reusable cover sheet 500, upper layer 510 and lower layer 530 can be configured so that they may be laundered for disinfection.

Support mattress 560 can be any configuration known in the art for supporting person 180. For example, in certain exemplary embodiments, support mattress 560 may be an alternating-pressure-pad-type mattress or other type of mattress utilizing air to inflate or pressurize a cell or chamber within the mattress. In other exemplary embodiments, support mattress 160 does not utilize air to support person 180.

As one of ordinary skill in the art will appreciate, vapor and air can carry organisms such as bacteria, viruses, and other potentially harmful pathogens. As such, and as will be described in more detail herein, in some embodiments of the present disclosure, one or more antimicrobial devices, agents, etc., can be provided to prevent, destroy, mitigate, repel, trap, and/or contain potentially harmful pathogenic organisms including microbial organisms such as bacteria, viruses, mold, mildew, dust mites, fungi, microbial spores, bioslimes, protozoa, protozoan cysts, and the like, and thus, remove them from air and from vapor that is dispersed and removed from the patient and from the environment surrounding the patient. In addition, in various embodiments, the cover sheet 500 can include various layers having antimicrobial activity. In some embodiments, for example, top, middle and bottom layers, 510, 520 and 530 can include particles, fibers, threads, etc., formed of silver and/or other antimicrobial agents.

In various exemplary embodiments, middle layer 520 can be formed of various materials, and can have a number of configurations and shapes, as described herein. In some embodiments, the material is flexible. In such exemplary embodiments, the flexible material can include properties that resist compression, such that when the flexible material is compressed, for example, by the weight of a patient lying on cover sheet 500, the flexible material has a tendency to return toward its original shape, and thereby impart a supportive function to cover sheet 500. The flexible material can also include a property that allows for lateral movement of air through the flexible material even under compression.

Examples of materials that can be used to form middle layer 520 can include, but are not limited to, natural and synthetic polymers in the form of particles, filaments, strands, foam (e.g., open cell foam), among others, and natural and synthetic materials such as cotton fibers, polyester fibers, and the like. Other materials can include flexible metals and metal alloys, shape memory metals and metal alloys, and shape memory plastics. These materials can include elastic, super elastic, linear elastic, and/or shape memory properties that allow the flexible material to flex and bend and to form varying shapes under varying conditions (e.g., compression, strain, temperature, etc.).

FIGS. 4A-4D illustrate exemplary various embodiments of a flexible spacer material that may be used in middle layer 520. In various embodiments of FIGS. 4A-4D, the spacer material can include a number of cross-sectional geometric shapes, including but not limited to, circular, ovular, polygonal, and irregular geometric shapes. For example, as shown in FIGS. 4A-4D, the spacer material can include a strand member 525, a foam member 526, a coil member 527, or a convoluted member 528, or a combination thereof, each having a circular cross-sectional shape. It is understood that the disclosed spacer materials are merely exemplary, and that other embodiments may comprise different spacer materials, including for example, a knitted spacer, or a combination of glass fiber and knitted textile. Each of the embodiments illustrated in FIGS. 4A-4D, either alone, or in combination, can provide support to the patient lying on cover sheet 500, can aid in lowering interface pressures between the patient and cover sheet 500, and can permit air to flow under patient 180. In addition each of the embodiments can function in combination with a support platform or support surface, such as an air mattress, to further reduce interface pressures between patient 180 and cover sheet 500.

In each of FIGS. 4A-4D, the flexible material includes a first and a second end 521 and 523. In various exemplary embodiments, first and second ends 521 and 523 can include surfaces and/or structures that allow them to connect to upper layer 510 and bottom layer 520 and bond or seal second layer 520 to top and bottom layers 510 and 530.

Figure 5A:
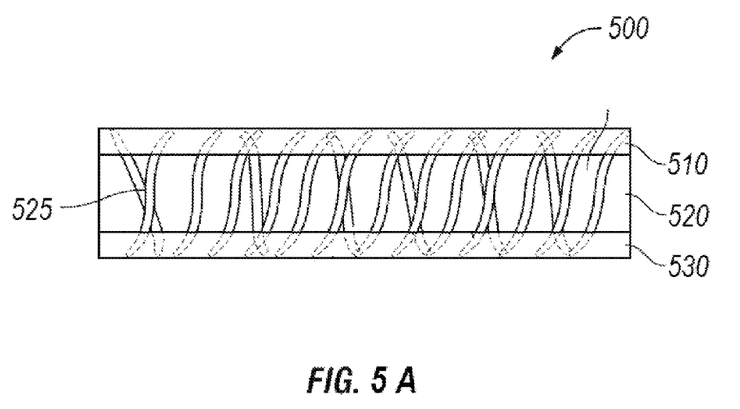
FIGS. 5A-5B illustrate various exemplary embodiments of a spacer material bonded to top and bottom layers of the cover sheet of FIG. 1.
Figure 5B:
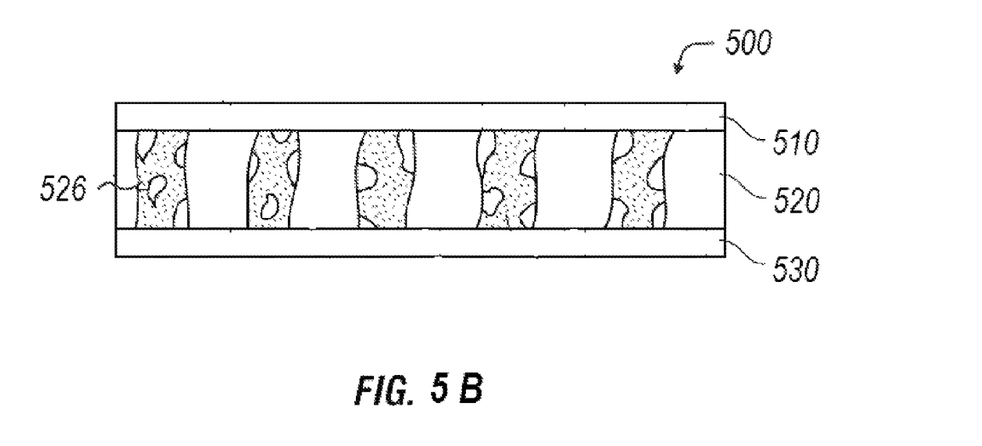

FIGS. 5A-5B illustrate how strand members 525 and foam members 526, respectively, may be coupled to top and bottom layers 510 and 530. Air flow 541 (not shown in these figures for purposes of clarity) can then flow between and/or through strand members 525 and foam members 526. In various exemplary embodiments of FIGS. 5A-5B, strand members 525 and foam members 526 of middle layer 520 can be chemically attached to the top and bottom layers 510 and 530 through the use of adhesives, and the like, and/or mechanically attached through the use of fasteners such as stitches, clasps, hook and loop, and the like, and/or physically attached through the use of welds, such as radio-frequency (RF) welds, ultrasonic energy (i.e., ultrasonic welding) and related methods. As described herein, the shapes and sizes of the top, middle, and bottom layers of exemplary embodiments of the multi-layer cover sheet can vary, and the exemplary embodiments illustrated in the figures are not limited to rectangular shapes, as shown. Other shapes and sizes are contemplated and can be designed based upon the intended application of the multi-layer cover sheet. For example, in various exemplary embodiments, the shape and size of the cover sheet can be designed based upon the support surface or platform for which it is to be used, such as a chair.

In various exemplary embodiments, lower layer 530 can be formed of a variety of different materials that exhibit various properties. For example, lower layer 530 may be formed of a vapor impermeable, air impermeable, and a liquid impermeable material. The impermeable property of lower layer 530 prevents vapor, air, and liquid from passing through lower layer 530 and therefore, prevents exposure of the air, vapor, and liquid to a support surface or platform, on which cover sheet 500 is positioned. In addition, lower layer 530 can function as a guide to direct the air, vapor, and liquid toward the openings defined by portions of the perimeter not fastened together, or to direct air from the openings and toward an elongate member, as will be described herein. In various embodiments, lower layer 530 can also function as an attachment or coupling layer to attach the cover sheet 500 to a support surface or platform. For example, in various embodiments, the third layer can include extensions that can couple to the support surface such as a foam mattress. In such embodiments, the extensions can be wrapped around the support surface and tucked under the support surface or can be attached to the support surface using a variety of fasteners, such as those described herein. In other exemplary embodiments, the outer surface of the lower layer 530 can include a number of fasteners such as a hook and loop fasteners. In such exemplary embodiments, the support surface can be provided with a cover having a loop structure, and lower layer 530 can include an outer layer having a hook structure. Other methods and mechanisms are contemplated for attaching the multi-layer cover sheet to a support surface or platform so as to secure the multi-layer cover sheet thereto.

In various exemplary embodiments, cover sheet 500 can be a one-time use cover sheet or a multi-use cover sheet. As used herein, a one-time use cover sheet is a cover sheet for single-patient use applications that is formed of a vapor, air, and liquid permeable material that is disposable and/or inexpensive and/or manufactured and/or assembled in a low-cost manner and is intended to be used for a single patient over a brief period of time, such as an hour(s), a day, or multiple days. As used herein, a multi-use cover sheet is a cover sheet for multi-patient use that is generally formed of a vapor permeable, liquid impermeable and air permeable or air impermeable material that is re-usable, washable, can be disinfected using a variety of techniques (e.g., autoclaved, bleach, etc.) and generally of a higher quality and superior in workmanship than the one-time use cover sheet and is intended to be used by one or more patients over a period of time such as multiple days, weeks, months, and/or years. In various exemplary embodiments, manufacturing and/or assembly of a multi-use cover sheet can involve methods that are more complex and more expensive than one-time use coversheets. Examples of materials used to form one-time use cover sheets can include, but are not limited to, non-woven papers. Examples of materials used to form re-usable cover sheets can include, but are not limited to, Gore-Tex®, and urethane laminated to fabric.

The invention claimed is:

1. A cover sheet for placement between a person and a support surface comprising:
   a first end, a second end, a first side and a second side;
   an air mover;
   a first outer layer comprising a vapor permeable and air impermeable material, the first outer layer being configured to be placed adjacent the person;
   a second inner layer comprising a spacer material with a first surface facing the first outer layer and a second opposing surface, wherein the first and second surfaces extend between the first end, the second end, the first side and the second side; and
   a third outer layer comprising an air impermeable material, the third outer layer being configured to be placed adjacent the support surface, wherein:
     the second layer is between the first layer and the third layer;
     the air mover is configured to create air flow through the spacer material; and
     at least one of the first layer and third layer is bonded to the second layer across substantially the entire first surface of the second layer so as to minimize formation of spaces therebetween having lower flow resistance than a flow resistance through the second layer.

2. The cover sheet of claim 1 wherein at least one of the first layer and the third layer is adhesively bonded to the second layer across substantially the entire second surface of the second layer.

3. The cover sheet of claim 1 wherein the air mover is in fluid communication with a first aperture in the first or third layer.

4. The cover sheet of claim 3 wherein the first aperture is proximal to the first end of the cover sheet.

5. The cover sheet of claim 4 further comprising a second aperture in the first or third layer wherein the second aperture is proximal to the second end of the cover sheet.

6. The cover sheet of claim 1 wherein the air mover is proximal to the first end of the cover sheet and wherein the second layer is open to an outside environment proximal to the second end of the cover sheet.

7. The cover sheet of claim 1 wherein the air mover is configured to generate positive air pressure between the first layer and the third layer of the cover sheet.

8. The cover sheet of claim 1 wherein the first layer and the third layer are liquid impermeable.

9. The cover sheet of claim 1 wherein the spacer material comprises one of the following: open cell foam; natural or synthetic polymer particles, filaments, or strands; mesh; cotton fibers; polyester fibers; flexible metals and metal alloys; shape memory metals and metal alloys, and shape memory plastics.

10. The cover sheet of claim 1 further comprising an antimicrobial device proximal to the air mover.

11. The cover sheet of claim 1 wherein the spacer material comprises an antimicrobial agent.

12. The cover sheet of claim 1, wherein the air mover is configured to provide less than about 2.0 cubic feet per minute of air flow at a differential pressure of less than about 6.0 mm H2O.

13. The cover sheet of claim 1, wherein the air mover is configured to provide less than about 10.0 cubic feet per minute of air flow at a differential pressure of less than about 6.0 mm H2O.

14. The cover sheet of claim 1, wherein the air mover is configured to create noise levels of approximately 30.0 dB-A during operation.

15. The cover sheet of claim 1 wherein the air mover is a centrifugal fan.

16. The cover sheet of claim 1 further comprising an antimicrobial device proximal to the air mover.

17. The cover sheet of claim 16, wherein the air mover is integral with the cover sheet.

18. The support system of claim 16 wherein the spacer material is configured to permit air to flow through the spacer material while the spacer material supports a person laying on the cover sheet.

19. The cover sheet of claim 1, wherein:
   the first outer layer forms the top surface of the cover sheet; and
   the third outer layer forms the bottom surface of the cover sheet.

20. A method of removing moisture vapor from a person supported by a support surface, the method comprising:
   providing a cover sheet comprising:
     a first end, a second end, a first side and a second side;
     an air mover;
     a first outer layer comprising a vapor permeable and air impermeable material;
     a second inner layer comprising a spacer material with a first surface facing the first outer layer and a second opposing surface, wherein the first and second surfaces extend between the first end, the second end, the first side and the second side; and
     a third outer layer comprising an air impermeable material, wherein:
       the second layer is between the first layer and the third layer;
       the first layer is adhesively bonded to the second layer across substantially the entire first surface of the second layer;
       at least one of the first and third layer is bonded to the second layer across substantially the entire second surface of the second layer so as to minimize formation of spaces therebetween having lower flow resistance than a flow resistance through the second layer;
   placing the first outer layer of the cover sheet adjacent to the person;
   placing the third outer layer of the cover sheet adjacent the support surface; and
   operating the air mover to provide an air flow through the spacer material.

21. The method of claim 20 wherein the air flow is directed away from the air mover.

22. The method of claim 20 wherein the spacer material comprises one of the following: open cell foam; natural or synthetic polymer particles, filaments, or strands; mesh; cotton fibers; polyester fibers; flexible metals and metal alloys; shape memory metals and metal alloys, and shape memory plastics.

23. The method of claim 20 wherein the air mover is proximal to the first end and the air flow exits from the spacer material proximal to the second end.

24. The method of claim 20 wherein the air mover is integral with the cover sheet.

* * * * *